United States Patent [19]
Brumm

[11] Patent Number: 5,886,168
[45] Date of Patent: Mar. 23, 1999

[54] LOW D.E. STARCH CONVERSION PRODUCTS HAVING A SHARP DIFFERENTIATION IN MOLECULAR SIZE

[75] Inventor: Phillip J. Brumm, Rockford, Ill.

[73] Assignee: Enzyme Bio-Systems Ltd., Beloit, Wis.

[21] Appl. No.: 786,697

[22] Filed: Jan. 22, 1997

Related U.S. Application Data

[62] Division of Ser. No. 262,399, Jun. 20, 1994, Pat. No. 5,612,202, which is a continuation of Ser. No. 967,762, Oct. 28, 1992, abandoned.

[51] Int. Cl.$^6$ .......................... C08B 30/18; C08B 30/20; A61K 31/715; C12P 19/14
[52] U.S. Cl. ................. 536/103; 536/123.1; 536/123.12; 514/54; 514/58; 426/658; 426/661; 435/99; 435/101; 127/40
[58] Field of Search .................................. 536/103, 123.1, 536/123.12; 514/58, 54; 426/658, 661; 435/99, 101; 127/40

[56] References Cited

U.S. PATENT DOCUMENTS

| | | | |
|---|---|---|---|
| 3,756,919 | 9/1973 | Deaton | 127/40 |
| 3,849,194 | 11/1974 | Armbruster et al. | 127/29 |
| 3,853,706 | 12/1974 | Armbruster | 435/99 |

*Primary Examiner*—Francisco Prats
*Attorney, Agent, or Firm*—Norris, McLaughlin & Marcus

[57] ABSTRACT

Starch containing amylopectin is hydrolyzed with an alpha-amylase, preferably derived from *Bacillus stearothermophilus*, under conditions which cause a non-random cleavage of the starch molecules to yield fragments (molecules) having similar size and branching characteristics and a molecular weight range from about 20,000 to about 50,000 daltons are made. All of the desired molecules have ($\alpha$1,6) linkages. The hydrolysate is treated to enrich the concentration of the desired fragments and the enriched portion can be processed further to make a maltodextrin having a D.E. of less than about 8.

8 Claims, No Drawings

LOW D.E. STARCH CONVERSION PRODUCTS HAVING A SHARP DIFFERENTIATION IN MOLECULAR SIZE

This application is a division of application Ser. No. 08/262,399, filed Jun. 20, 1994, now U.S. Pat. No. 5,612, 202, which in turn was a continuation of Ser. No. 07/967, 762, filed Oct. 28, 1992, now abandonded.

BACKGROUND OF THE INVENTION

1. Field of the Invention

The present invention relates to a non-random starch hydrolysis process for preparing low D.E. starch hydrolysates and low D.E. starch conversion products, also known as low D.E. maltodextrins. D.E. is an abbreviation for dextrose equivalent, which is a common expression in the art for describing the total reducing sugars content of a material, expressed as percent dextrose, dry basis. The invention also has to do with the low D.E. maltodextrins themselves and to compositions employing them, such as fat mimetics and bulking agents.

2. Description of Related Art

Low D.E. starch hydrolysates and starch conversion products are known in the art. Generally they are produced by the hydrolysis of starch with acids or enzymes. Such products have a bland taste, low sweetness and low hygroscopicity and are useful for a variety of food applications. For example, they are useful as bulking agents, carriers, film-forming agents, encapsulating agents and the like. Typical of the early processes for preparing low D.E. starch hydrolysates are those described in U.S. Pat. Nos. 3,853,706 and 3,849,194. Both patents describe processes utilizing certain bacterial alpha-amylases to treat starch hydrolysates and provide products having a D.E. between 5 and 20–25.

U.S. Pat. No. 4,284,722 discloses the use of an alpha-anylase derived from *Bacillus stearothermophilus* to hydrolyze starch at a pH between 3.5 and 6.5 and a temperature between 100° and 115° C. for 160 minutes. Thereafter the temperature is dropped to 80°–100° C. prior to subsequent treatment with additional enzymes to prepare various end products.

U.S. Pat. No. 3,756,919 discloses the use of molecular extrusion to reduce a starch hydrolysate having a D.E. of from about 20 to about 43, to from about 5 to about 18. Molecular extrusion is an essential technique in that patent since the product being separated does not have a sharp differentiation in molecular size. The use of extrusion separation techniques is also described in U.S. Pat. Nos. 4,109, 075 and 4,840,807.

The known methods of starch hydrolysis by acids or enzymes cause random cleavage of the starch molecules. This results in the formation of linear and branched fragments of various chain lengths and properties. Depending on the chain length and degree of branching present, the resulting starch hydrolysate may be soluble or insoluble in water, may or may not be resistant to hazing, and so forth. Accordingly, a method of starch cleavage having more specificity is needed to prepare starch hydrolysates having more uniform and predictable qualities.

Various low D.E. maltodextrins are available commercially. For example, Maltrin M040 maltodextrin, available from Grain Processing Corporation, Muscatine, Iowa, is disclosed to have a D.E. of approximately 4–7. Nevertheless, there is a need for low D.E. hydrolysates having high concentrations of high molecular weight, branched molecules and having a reduced amount of high molecular weight linear molecules and low molecular weight linear or branched molecules. A means of making such low D.E. hydrolysates has now been developed according to the present invention. The hydrolysates of the invention have improved properties over other types of low D.E. hydrolysates such as lower color, higher clarity and cleaner taste than currently available products, and could be used in new applications such as stable, low D.E. syrups.

SUMMARY OF THE INVENTION

Starch containing amylopectin is hydrolyzed with an amylolytic enzyme that, under controlled conditions, causes limited cleavage of the amylopectin to yield high molecular weight branched fragments while cleaving any amylose present to soluble fragments. Soluble fragments generally are defined as those having a molecular weight less than about 5,000 daltons. Any alpha-amylase enzyme having the foregoing characteristics can be used in the process of the invention.

In the preferred embodiment of the invention, alpha-amylase derived from *Bacillus stearothermophilus* is employed under controlled conditions to cause non-random cleavage of the starch molecules. The objective is to obtain a starch hydrolysate having fragments of similar size and branching characteristics, particularly high molecular weight branched molecules having a molecular weight range of from about 20,000 to about 50,000 daltons. The concentration of the desirable fragments is then enriched in one or more stages.

The starch employed must contain amylopectin because amylopectin is hydrolyzed to the desired high molecular weight branched molecules. Starches having more than about 50% amylopectin are preferred. Starches having as little as 25% amylopectin or less can be employed, but they are undesirable because they give poor yields of the desired hydrolysate. Excellent results are obtained with starches from corn, wheat or rice, all of which contain about 70% or more amylopectin, and waxy corn, milo or other waxy starch which has up to about 98–100% amylopectin.

Amylose, another component of starches, is not branched, and its high molecular weight degradation products are insoluble. High amylose starches, therefore are not desirable.

Hydrolysis conditions are controlled according to the invention by employing high concentrations of starch and elevated temperatures. Following hydrolysis, the enzyme is inactivated and the high molecular weight branched molecules are enriched to make a maltodextrin having a D.E. of less than about 8, preferably from about 0.1 to about 8.

DESCRIPTION OF THE PREFERRED EMBODIMENTS

In the preferred embodiment of the invention, starch containing amylopectin is slurried at a high concentration of from about 20% to about 50% dry substance (hereinafter "d.s."), preferably from about 25% to about 40% d.s., and is contacted with a *Bacillus stearothermophilus* alpha-amylase for from about 2 to about 30 minutes at an elevated temperature of from about 102° C. to about 112° C., optionally followed by further incubation for from about 1 to about 90 minutes at a temperature of from about 90° C. to about 100° C., to cause non-random cleavage of the starch. A liquefact is thereby produced that contains a fraction comprised of high molecular weight branched molecules having a molecular weight distribution of from about 20,000 to about 50,000 daltons and a D.E. of from about 10 to about 30.

The branched molecules are comprised of glucose polymers which are predominantly linked at the (α1,4) position, but which also contain (α1,4)-linked chains connected to a backbone via (α1,6) linkages. It is believed that the (a1,6) linkages in the branched molecules are responsible for the unique properties of the products of the invention. Previously known low D.E. maltodextrins have other linkages which cause gelling and retrogradation.

The enzyme is then inactivated by adjusting the pH to from about 3.5 to about 4.5 and maintaining a temperature from about 60° C. to about 100° C. for from about 10 to about 240 minutes.

Then the liquefact is treated to remove insoluble materials, most of which are proteins and fats. A variety of methods can be used such as filtration through diatomaceous earth on a fixed or rotary vacuum filter, microporous filtration through a ceramic or polymer membrane, centrifugation, flocculation, flotation and the like. The clarified liquefact is then subjected to ultrafiltration by passing it through an ultrafiltration unit containing membranes with molecular weight cutoff values (as specified by the manufacturer) of from about 3,000 to about 30,000 daltons. The permeate of ultrafiltration, containing predominantly (80% to 100% by weight of solids) low molecular weight material is collected separately, and the ultrafiltration retentate containing from about 70% to about 100% high molecular weight (about 20,000 to about 50,000 daltons) material is collected as the product. The separation is deemed adequate when high pressure liquid chromatography (HPLC) analysis of the retentate indicates that the desired distribution of high and low molecular weight fractions has been achieved.

A variety of ultrafiltration methods can be used successfully to-achieve the desired product split. A batch process can be used, where retentate material is recycled through the ultrafiltration unit until the desired high molecular weight concentration is reached. Alternately, the material may be processed continuously in a single pass to achieve the desired separation. The type of process used is determined by the other operating parameters, such as selectivity of the membrane, flow rate through the ultrafiltration unit, and the area of the ultrafiltration membranes in use, as will be apparent to those skilled in the art.

The final product optionally can be spray dried to a powder.

The maltodextrins of the invention, whether in the form of syrups or dry powder, are characterized by blandness of taste and low sweetness. When used in food products, they have a minimal effect upon flavor while providing bulk, stability, favorable mouthfeel characteristics and increased nutritive value. The maltodextrins are especially characterized by their low color, high clarity and clean taste and. Among other things, they can be used in stable, low D.E. syrups.

These characteristics make the products of the invention particularly suitable for applications as carriers for coloring agents, flavors, essences and synthetic sweeteners; spray drying adjuncts for coffee extracts and tea extracts; bulking, bodying and dispersing agents in synthetic creams or coffee whiteners; ingredients promoting a moisture retention in bread, pastry and meats; components of dry soup mixes, bakery mixes, frosting mixes, spice mixes and blends, beverage powders, condiments, gravy mixes, sauce mixes and frozen dairy foods; and in fat mimetics. In addition, they are useful in the formulation of tableting compounds which can be used in food products or pharmaceutical products, anti-caking agents, whipped products, protective coatings, agglomeration aids, low or reduced-in-calorie foods and beverages, and low or reduced-in-fat foods and beverages.

EXAMPLES

The approximate molecular weight of the high molecular weight material was determined by size exclusion chromatography. Samples of pullulan with known molecular weights between 5,000 and 800,000 daltons (Shodex Standard P-82 from Showa Denko K.K., Specialty Chemical Division, Shodex (Separation & HPLC) Group, 13–9, Shiba Daimon 1-chome, Minato-ku, Tokyo 105, Japan, distributed by Phenomenex Inc., 2320 W. 205th Street, Torrance, Calif. 90501 U.S.A.) are chromatographed separately using the ShoDex KB802.5 column and the given conditions. A linear relationship is obtained between the elution time of the pullulan and the log of its molecular weight. From this linear relationship, the log of the molecular weight of the maltodextrin peaks are obtained using the retention time of the individual maltodextrin peaks. The high molecular weight material has a retention time of 5.1 minutes which corresponds to 20,000 to 50,000 daltons. This fraction corresponds to 70% to 100% of the material as determined by refractive index using an area percent integration. The remaining material has a retention time of 7.45 minutes, which corresponds to a molecular weight of less than 5000 daltons. No intermediate molecular weight material is detectable.

The branched nature of the high molecular weight material was demonstrated by treatment of the high molecular weight material with enzymes which cleave only (α1,6) linkages. The high molecular weight material was treated with either *Pseudomonas amyloderamosa* isoamylase (Hayashyibara Biochemical Laboratories, Inc., 1-2-3 Shimoishii, Okayama, 700 Japan) or purified rice debrancher (Jiro Yamada, "Purification of Debranching Enzyme from Mature Ricer Seeds", *Agricultural and Biological Chemistry*, 45 (1981), pp. 1269–1270). Treatment of the material with either of these two enzymes completely abolished the peak at 5.1 minutes, indicating that all of the material in this peak contained (α1,6) linkages.

Example 1

Corn starch (containing 72% w/w amylopectin) at 32.9% d.s., and containing 135 ppm $Ca^{++}$ on a starch dry basis (hereinafter "d.b."), was adjusted to pH 6.2 with $Na_2CO_3$. To this slurry was added 3.0 units per gram (hereinafter "u/g") d.s starch of *Bacillus stearothermophilus* enzyme sold by Enzyme Bio-Systems Ltd. as G995 alpha-amylase (assayed as described in Brumm, P. J. and Teague, W. M., A Reduced Stability *Bacillus stearothermophilus* α-Amylase for Food Applications, *Biotechnology Letters*, 10, (1988) pp. 445–450). The slurry was passed through a jet cooker at a temperature of 225° F. for a residence time of 5.1 minutes. The material was flashed to atmospheric pressure and incubated for 90 minutes at 208° F. The D.E. of the liquefied solution was about 16. The pH was then reduced to 3.5 and the solution was held for 240 minutes at 150° F. to inactivate the enzyme.

In order to remove insoluble fat and protein, the starch hydrolysate was filtered at 60° C. through a bed of Eagle Picher FW 40 diatomaceous earth (Eagle Picher Minerals, Inc., P.O. Box 12130, Reno, Nev. 89510 U.S.A.) using a rotary vacuum filter. The resulting clear filtrate was subject to ultrafiltration using an Advanced Membrane Technology AES-30 membrane (Advanced Membrane Technology, 1305 Calvary Church Road, Gainesville, Ga. 30507 U.S.A.) to provide a retentate containing 60% by weight of a starch hydrolysate having a molecular weight of greater than 20,000. Then the filtrate was diafiltered (i.e., diluted following ultrafiltration and subject to further ultrafiltration) twice to provide a product containing 85% by weight of the greater than 20,000 molecular weight material and having a D.E. of 3.5. The material was spray dried using a conventional spray drying nozzle in a tower dryer at 180° F. wet bulb to provide a powdered solid.

Example 2

Corn starch (containing 72% w/w amylopectin) at 35.5% d.s., and containing 100 ppm $Ca^{++}$ on a starch d.b., was adjusted to pH 6.0. To this slurry was added 3.6 u/g d.s starch of G995 alpha-amylase. The slurry was passed through a jet cooker at a temperature of 225° F. for a residence time of 3.8 minutes. The material was flashed to atmospheric pressure and incubated for 90 minutes at 211° F. The D.E. of the liquefied solution was about 15. The pH was then reduced to 3.5 and the solution was held for 240 minutes at 160° F. to inactivate the enzyme.

The starch hydrolysate was filtered to remove fat and protein, and the filtrate was subjected to ultrafiltration using an Advanced Membrane Technology AES-05 membrane to provide a retentate containing 78% by weight of a starch hydrolysate having a molecular weight of greater than 20,000 and having a D.E of 4.7. The material was spray dried in a tower dryer to provide a powdered solid.

Example 3

A 500 g slurry of 30.0% d.s. corn starch (containing 72% w/w amylopectin) containing 100 ppm $Ca^{++}$ on a starch d.b., was adjusted to pH 6.2. To this slurry was added 3.0 u/g d.s starch of G995 alpha-amylase. The slurry was held at 208° F. for 60 minutes. The D.E. of the liquefied solution was about 15.

The pH was then reduced to 3.5 with hydrochloric acid to inactivate the enzyme. The starch hydrolysate was filtered to remove fat and protein, and the filtrate was subjected to ultrafiltration using an Amicon YM-10 membrane (available from Amicon, Inc., 72 Cherry Hill Drive, Beverly, Mass. 01915 U.S.A.) to provide a retentate containing 59% by weight of a starch hydrolysate having a molecular weight of greater than 20,000. Then the filtrate was diafiltered once to provide a product containing 76% by weight of the greater than 20,000. molecular weight material and having an approximate D.E. of 6.4.

Example 4

A 500 g slurry of 25.0% d.s. corn starch (containing 72% w/w amylopectin) containing 100 ppm $Ca^{++}$ on a starch d.b., was adjusted to pH 6.2. To this slurry was added 3.0 u/g d.s starch of G995 alpha-amylase. The slurry was held at 208° F. for 60 minutes. The D.E. of the liquefied solution was about 14.

The pH was then reduced to 3.5 with hydrochloric acid to inactivate the enzyme. The starch hydrolysate was filtered to remove fat and protein, and the filtrate was subjected to ultrafiltration using an Amicon YM-10 membrane to provide a retentate containing 65% by weight of a starch hydrolysate having a molecular weight of greater than 20,000 and having an approximate D.E. of 7.1

Example 5

A 500 g slurry of 30.0% d.s. waxy corn starch (containing about 100% w/w amylopectin) containing 100 ppm $Ca^{++}$ on a starch d.b., was adjusted to pH 6.2. To this slurry was added 1.3 u/g d.s starch of G995 alpha-amylase. The slurry was held at 208° F. for 60 minutes. The D.E. of the liquefied solution was about 8.3.

The pH was then reduced to 3.5 with hydrochloric acid to inactivate the enzyme. The starch hydrolysate was filtered to remove fat and protein, and the filtrate was subjected to ultrafiltration using an Amicon YM-10 membrane to provide a retentate containing 80% by weight of a starch hydrolysate having a molecular weight of greater than 20,000. Then the filtrate was diafiltered once to provide a product containing 96% by weight of the greater than 20,000 molecular weight material and having an approximate D.E. of 2.6.

Example 6

A 500 g slurry of 25.0% d.s. wheat starch (containing 72% w/w amylopectin) containing 100 ppm $Ca^{++}$ on a starch d.b., was adjusted to pH 6.2. To this slurry was added 3.0 u/g d.s starch of G995 alpha-amylase. The slurry was held at 208° F. for 60 minutes. The D.E. of the liquefied solution was about 18.3.

The pH was then reduced to 3.5 to inactivate the enzyme. The starch hydrolysate was filtered to remove fat and protein, and the filtrate was carbon refined by treatment with 1% w/v activated granular carbon in a beaker at 60° C. for 60 minutes. The carbon was removed by filtration using Whatman 1 filter paper (Whatman Paper Ltd., Springfield Mill, Maidstone, Kent ME14 2LE, England, and Whatman Lab Sales, P.O. Box 1359, Hillsboro, Oreg. 97123, U.S.A.) and the filtrate was subjected to ultrafiltration using an Amicon YM-10 membrane to provide a retentate containing 80% by weight of a starch hydrolysate having a molecular weight of greater than 20,000 and having an approximate D.E. of 5.6.

Example 7

A 500 g slurry of 25.0% d.s. rice starch (containing 83% w/w amylopectin) containing 100 ppm $Ca^{++}$ on a starch d.b., was adjusted to pH 6.2. To this slurry was added 3.0 u/g d.s starch of G995 alpha-amylase. The slurry was held at 208° F. for 60 minutes. The D.E. of the liquefied solution was about 18.3.

The pH was then reduced to 3.5 to inactivate the enzyme. The starch hydrolysate was filtered to remove fat and protein, and the filtrate was carbon refined by treatment with 1% w/v activated granular carbon. The carbon was removed by filtration, and the filtrate was subjected to ultrafiltration using an Amicon YM-10 membrane to provide a retentate containing 80% by weight of a starch hydrolysate having a molecular weight of greater than 20,000. Then the filtrate was diafiltered once to provide a product containing 96% by weight of the greater than 20,000 molecular weight material and having an approximate D.E. of 5.0.

Approximate D.E. values were determined by osmometry according to the method of Fitton (Fitton M. G., Rapid Determination of Dextrose Equivalent by Cryoscopy, *Starch/Starke*, 31, (1979) pp. 381–384). Samples were diluted to 15% carbohydrate dry substance and the osaolality of the solution was determined by freezing point depression osmometry using an Advanced DigiMatic Osmometer Model 3D2 (Advanced Instruments, Inc., 1000 Highland Avenue, Needham Heights, Mass. 02194 U.S.A.). Approximate D.E. values are equal to millOsms/10; the D.E. value is corrected for the ash contribution in non-diafiltered samples by subtracting 1.5 D.E.

Aqueous solutions containing 10% by weight of each maltodextrin were filtered through either a 0.22 or 0.45 micron membrane and analyzed by gel permeation chromatography on HPLC using a ShowDex KB802.5 column (8 mm×300 mm). Operating conditions were as follows: ambient temperature, 1.0 ml/min flow rate, water as mobile phase, and sample size of 20 microliters. Peaks were detected using a Shimadzu RID-6A Refractive Index Detector (Shimadzu Corp., 7102 River Drive, Columbia, Md. 20142 U.S.A.); and peak areas were determined using a Shimadzu C-R5A integrator and reported as area percent.

Example 8

A 500 g slurry of 30.0% d.s. corn starch (containing 72% w/w amylopectin) containing 100 ppm $Ca^{++}$ on a starch d.b., was adjusted to pH 6.2 with $Na_2CO_3$. To this slurry was added 10.0 u/g d.s starch of G995 alpha-amylase. The slurry was held at 230° F. for 10 minutes. The D.E. of the liquefied solution was about 17.

The pH was then reduced to 3.5 with hydrochloric acid and maintained at 90° C. for 30 minutes to inactivate the enzyme.

The starch hydrolysate was filtered to remove fat and protein, and the filtrate was subjected to ultrafiltration using an Amicon YM-10 membrane to provide a retentate containing 71% by weight of a starch hydrolysate having a molecular weight of greater than 20,000. Then the filtrate was diafiltered once to provide a product containing 95% by weight of the greater than 20,000 molecular weight material and having an approximate D.E. of 2.6.

Comparative Example

Molecular weight distribution of the 3.5 D.E. maltodextrin prepared according to Example 1 was compared with Maltrin M040 and Maltrin M100 produced by Grain Processing Corporation, Muscatine, Iowa 52761. Aqueous solutions containing 10% by weight of each maltodextrin were filtered through 0.45 micron membranes and analyzed by gel permeation chromatography. The chromatograms revealed the maltodextrin of Example 1 contained 80% of a high molecular weight component (20,000 to 50,000 daltons) and 20% of a low molecular weight material (less than 3,000 daltons). The Maltrin M040 contained approximately 54% of the high molecular weight material and the remaining 46% had a wide range of molecular weights between about 20,000 and 200 daltons. The Maltrin M100 contained approximately 41% of the high molecular weight material with the remaining 59% having a wide range of molecular weights between about 20,000 and 200 daltons.

The resistance to haze formation and retrogradation of the 3.5 D.E. maltodextrin prepared according to Example 1 was compared with Maltrin M040. Aqueous solutions containing 40% by weight of each maltodextrin were prepared by heating and stirring the solutions. The two solutions were stored at room temperature (25° C.). The M040 solution became opaque and solid within 24 hours; the solution of maltodextrin from Example 1 remained clear and liquid for greater than 90 days.

The maltodextrin prepared according to Examples 1, 6 and 7 were compared with Maltrin M040 and Maltrin M100. Aqueous solutions containing 50% by weight of each dry maltodextrin were prepared by heating and stirring the solutions; the liquid maltodextrins of Examples 6 and 7 were adjusted to 50% d.s. by addition of water. The Maltrin M040 became opaque upon cooling to room temperature and solidified within 60 minutes. The other solutions were stored at room temperature (25° C.) to determine stability toward retrogradation and hazing. The Maltrin M100 became opaque and semi-solid within 24 hours. The solutions prepared according to Examples 1, 6 and 7 remained clear for over 7 days.

The maltodextrin of Example 1 also was analyzed to determine descriptive ratio and iodine absorbency. The descriptive ratio was 2.4 and iodine absorbency was 0.98.

All percentages recited herein are by weight (w/w) unless specified otherwise, such as by volume (w/v). All molecular weights herein are expressed in daltons.

Having set forth a description of the invention and some specific examples, the scope is now more particularly set forth in the appended claims.

What is claimed is:

1. A starch conversion product consisting essentially of:

a) from about 70% to 96% of a maltodextrin having branched molecules and a molecular weight from about 20,000 to about 50,000 daltons, and b) a maltodextrin having a molecular weight of less than 5,000 daltons, the starch conversion product having a D.E. of less than about 8, made by a process which comprises the sequential steps of:

a) contacting an aqueous slurry comprising from about 20% to about 50% d.s. of a starch having more than about 50% amylopectin with a *Bacillus stearothermophilus* alpha-amylase designated as G995 which cleaves amylopectin to make branched molecules having a molecular weight distribution of from about 20,000 to about 50,000 daltons and cleaves amylose to a molecular weight less than about 5,000 daltons at a temperature from about 102° C. to about 112° C. for from about 2 to about 30 minutes to make a liquefact having a D.E. of from about 10 to about 30;

b) inactivating the alpha-amylase by adjusting the pH to from about 3.5 to about 4.5 and maintaining a temperature of from about 60° C. to about 100° C. for from about 10 to about 240 minutes;

c) removing insoluble materials from the liquefact; and d) filtering the maltodextrin from the liquefact.

2. The product of claim 1 wherein the liquefact prepared by step a) is subject to incubation for from about 1 to about 90 minutes at a temperature of from about 90° C. to about 100° C.

3. The product of claim 1 wherein filtering in step d) is by ultrafiltration.

4. A high molecular weight, low D.E. starch conversion product derived from an amylopectin-containing starch which product consists essentially of:

a) from about 70% to 96% of a maltodextrin having branched molecules with ($\alpha$1,6) linkages and a molecular weight from about 20,000 to about 50,000 daltons, and b) a maltodextrin having a molecular weight of less than 5,000 daltons, the starch conversion product having a D.E. of less than about 8.

5. The product of claim 4 which is in the form of a syrup.

6. The product of claim 4 which is in the form of a powder.

7. An edible product for human or animal consumption employing as an ingredient thereof a starch conversion product consisting essentially of:

a) from about 70% to 96% of a maltodextrin having branched molecules with (α1,6) linkages and a molecular weight from about 20,000 to about 50,000 daltons, and b) a maltodextrin having a molecular weight of less than 5,000 daltons, the starch conversion product having a D.E. of less than about 8.

8. A pharmaceutical product employing as an ingredient thereof a starch conversion product consisting essentially of:

a) from about 70% to 96% of a maltodextrin having branched molecules with (α1,6) linkages and a molecular weight from about 20,000 to about 50,000 daltons, and b) a maltodextrin having a molecular weight of less than 5,000 daltons, the starch conversion product having a D.E. of less than about 8.

* * * * *